United States Patent
Kirsch et al.

(10) Patent No.: US 8,612,008 B2
(45) Date of Patent: Dec. 17, 2013

(54) MICROCURRENT AND CRANIAL ELECTROTHERAPY STIMULATOR FOR CONTROL OF ANXIETY, INSOMNIA, DEPRESSION AND PAIN

(75) Inventors: Daniel L. Kirsch, Mineral Wells, TX (US); Sai Cheong Chan, West Kowloon (HK)

(73) Assignee: Electromedical Products International, Inc., Mineral Wells, TX (US)

( * ) Notice: Subject to any disclaimer, the term of this patent is extended or adjusted under 35 U.S.C. 154(b) by 761 days.

(21) Appl. No.: 12/588,647

(22) Filed: Oct. 22, 2009

(65) Prior Publication Data
US 2010/0145410 A1    Jun. 10, 2010

Related U.S. Application Data

(60) Provisional application No. 61/193,034, filed on Oct. 23, 2008.

(51) Int. Cl.
*A61N 1/00* (2006.01)

(52) U.S. Cl.
USPC .................................. 607/46; 607/2

(58) Field of Classification Search
USPC ...................... 607/2, 63, 45–46, 23
See application file for complete search history.

(56) References Cited

U.S. PATENT DOCUMENTS

| | | | | |
|---|---|---|---|---|
| 5,332,401 | A * | 7/1994 | Davey et al. | 607/116 |
| 5,458,625 | A | 10/1995 | Kendall | |
| 6,108,580 | A * | 8/2000 | Greenspan et al. | 607/74 |
| 7,283,869 | B2 * | 10/2007 | Onda et al. | 600/547 |
| 7,840,272 | B2 * | 11/2010 | Kronberg et al. | 607/51 |
| 8,428,735 | B2 * | 4/2013 | Littlewood et al. | 607/46 |
| 2004/0230256 | A1 | 11/2004 | Lin-Hendel | |
| 2005/0021104 | A1 | 1/2005 | DiLorenzo | |
| 2006/0241719 | A1 * | 10/2006 | Foster et al. | 607/45 |
| 2007/0142862 | A1 | 6/2007 | DiLorenzo | |
| 2007/0250119 | A1 | 10/2007 | Tyler et al. | |
| 2007/0276449 | A1 * | 11/2007 | Gunter et al. | 607/46 |
| 2007/0299472 | A1 * | 12/2007 | Brighton | 607/2 |
| 2008/0288016 | A1 * | 11/2008 | Amurthur et al. | 607/44 |
| 2011/0184488 | A1 * | 7/2011 | De Ridder | 607/46 |

FOREIGN PATENT DOCUMENTS

| | | |
|---|---|---|
| WO | WO2007/138368 | 12/2007 |
| WO | WO2008/059488 | 5/2008 |

* cited by examiner

*Primary Examiner* — Christopher D Koharski
*Assistant Examiner* — Catherine Voorhees
(74) *Attorney, Agent, or Firm* — Welsh Flaxman & Gitler LLC (57) ABSTRACT

A device for controlling anxiety, insomnia, depression and pain utilizing a microcurrent and cranial electrotherapy stimulation. The device could also be utilized to treat other types of stress-related disorders. A relatively low level current having a particular frequency is produced by the device in two channels wherein the current for both of the channels can be different. Electrodes are placed at various points of the patient's body to relieve pain. When utilized to control anxiety, insomnia and depression, a single channel is produced which is applied to the patient's ear lobes by two ear clips.

10 Claims, 7 Drawing Sheets

FLOW OF THE TREATMENT CURRENT

Flow of current is either A>B>C>D>E>F>G>H>I>J>K>L>M>N>O>P>Q>R>S>T
or T>S>R>Q>P>O>N>M>L>K>J>I>H>G>F>E>D>C>B>A

MICROCURRENT AND CRANIAL ELECTROTHERAPY STIMULATOR FOR CONTROL OF ANXIETY, INSOMNIA, DEPRESSION AND PAIN

CROSS-REFERENCE TO APPLICATION(S)

The present application claims the priority of U.S. provisional patent application Ser. No. 61/193,034, filed on Oct. 23, 2008, and is incorporated herein by reference.

FIELD OF THE INVENTION

The present invention is directed to a system and method for controlling anxiety, insomnia, depression and pain utilizing a microcurrent and cranial electrotherapy stimulator.

BACKGROUND OF THE INVENTION

The application of electromedical currents is not a new concept. Ancients recognized the therapeutic value of naturally occurring electrical phenomena long before William Gilbert defined electricity in 1600. Both Aristotle and Plato referred to the Black Torpedo (electric ray fish) prescribed in 46 AD by the physical Scribonius Largus for the relief of a variety of medical conditions from headaches to gout (head to foot). In the 1800s dentists reported pain reduction using early and somewhat crude electromedical devices.

By the late 1800s electrical devices were in widespread use to manage pain and claimed to cure a variety of medical disorders. The exuberant claims of unrefined early electrical technologies facilitated by the political clout of the pharmaceutical lobbies caused this form of therapy to fall into disrepute by the medical profession in the early part of the 20th century. As a result, medical colleges stopped teaching electrotherapeutics. Biophysics was virtually eliminated from medical practice leaving chemistry as the master science and with it the burden of responsibility for curing all disease. Now, in the 21st century it is clear that chemistry as the sole therapeutic model for medicine has not lived up to its promise causing modern medicine to reexamine the potential of biophysics.

Experimentation with low intensity electrical stimulation of the brain was first reported by Drs. Leduc and Rouxeau of France in 1902. Initially, this method was called electrosleep as it was thought to be able to induce sleep. Research on using what is now referred to as Cranial Electrotherapy Stimulation (CES) for treatment of anxiety, insomnia and depression began in the Soviet Union during the 1950s and first came to the United States in the 1960s.

In 1965 Drs. Ronald Melzack of Canada and Patrick Wall of the United Kingdom published a paper explaining a new comprehensive theory of how pain is processed by the nervous system. Their Gate Control theory also explained how electrical stimulation can influence the physiology of pain pathways. By 1967 electrical devices were surgically implanted to control severe low back pain. Surface electrical stimulation devices were used to test the person's response as a means of screening surgical candidates and to determine the most effective electrode site for implantation. It was soon discovered that electromedical treatment through the skin (transcutaneous) was equally effective and could be used for pain relief alone, avoiding surgery. Since then, these devices, known as transcutaneous electrical nerve stimulators (TENS) have become widely accepted by health care practitioners to control many forms of pain. TENS technology is based on the concept of using electricity as an overriding force. Repeatedly tapping a painful area with a blunt object, such as a pen or a spoon might produce a similar effect. That is why TENS is referred to as counter-irritation analgesia. There is virtually no residual effect with TENS and the people who use it develop a tolerance to electrical therapy.

All life is of an electrochemical nature. There are extensive electrical fields at work throughout the universe and the body. The nervous system, for example, has long been known to work through both electrochemical and purely electrical signals. In fact, all molecules are held together by electrical bonding at the atomic level. Basic science research into the nature of bioelectrical control systems in humans and animals led medical scientists such as Dr. Robert O. Becker of the United States and Dr. Björn Nordenström of Sweden (who served as Chairman of the Nobel Assembly), to propose completely new theories of physiology based on our latest understanding of biophysics.

Alpha-Stim® technology incorporates these theories and is proven more efficacious than most other treatments for the conditions it treats. It is a viable alternative to traditional TENS, as well as an alternative or complementary treatment with pharmacological management, surgery and other interventions. The original Alpha-Stim® Model 2000 weighed 40 pounds and cost $5,850 when it was first introduced in 1981. The Alpha-Stim® M microcurrent stimulator utilizes the most advanced technology available today. It is now possible, in most cases, to alleviate anxiety, insomnia, depression and pain with far less current than used in previous technologies, and experience long term and cumulative relief with as little as only a few minutes of treatment progress.

SUMMARY OF THE INVENTION

The deficiencies of the prior art are addressed by the present invention which is directed to a method and system for controlling pain using microcurrent electrical therapy (MET) which is a term used to describe low level current use for pain control by producing a waveform introduced to the body of the individual in areas proximate to the pain utilizing the appropriate probe or electrodes. This system is distinguished from previous forms of transcutaneous electrical nerve simulation (TENS) since MET uses far less current, but delivers the current in much longer pulses. Whereas the TENS devices must be constantly worn because they offer virtually no residual effect, the MET devices effects are long lasting and cumulative. This same device is utilized to control anxiety, insomnia and depression. When used to treat pain, the MET device would utilize a pair of electrodes in contact with various parts of the body. When used to treat anxiety, insomnia and depression, the MET device would employ a pair of electrodes in contact with the patient's ear lobes. This type of treatment is known as cranial electrotherapy stimulation (CES). Additionally, one of the embodiments of the present invention would be used exclusively for CES treatment by the application of pulsed waves applied to a subject's ear through the use of the ear clip electrodes.

Results in electromedicine are based on the design of the waveform, the amount of current, the location of the electrodes, and the amount of time used. The MET device is a microcomputer incorporating the latest advances in solid state electronics. All components are of the highest quality available to assure the user reliable and trouble-free performance. The design assures electrical safety by the use of readily available 1.5 volt AA batteries.

The MET device is a precision technology which generates a modified square, bipolar waveform of 0.5, 1.5, or 100 pulses per second (Hz), at 50 to 600 microamperes (1 μA is one-millionth of an ampere), in a 50% duty cycle.

The MET device is small, compact and lightweight. It was designed to be versatile. It can be used in a health care practitioner's office, clinic or hospital, for portable and quick response needs such as emergency medical or military applications, as well as for self-administered treatment at home on a scheduled or as-needed basis.

The controls are fully digital for precision, consistency and reliability and at the same time simple and easy to operate. An adjustable timer and a locking option that freezes the treatment time, frequency and current assures the prescribed treatment waveform and dosage even if the user is distracted or fall asleep. The amount of current can easily be decreased to assure comfort or increased to reduce treatment time.

The MET device, according to the present invention, would apply low level current to control an individual's pain through the use of various probes or electrodes. One type of probe is described in U.S. patent application Ser. No. 12/219,878, listing Daniel L. Kirsch as the inventor and is incorporated herein by reference. The MET device, as previously indicated, is distinguished from the TENS device since the MET device uses far less current, but delivers the current in much longer pulses.

The MET device includes an electronic circuit which operates to maintain a nearly constant current flow to the electrodes, thereby minimizing the effects of electrode resistance variations. The MET device continuously performs self-diagnostics to insure that all aspects of the circuitry are always working properly, and that the electrodes are making adequate contact with the skin. Additionally, the present invention utilizes a lock, auto-off timers and alarms that would worn the patient if an electrode is not properly placed on the body.

The second embodiment of the present invention is directed to a cranial electrotherapy stimulator (CES) which utilizes a minimal amount of current in relatively long pulses to control the anxiety, insomnia and depression of various patients by applying these pulses to the patient through the use of a pair of ear clip electrodes. It is noted that the MET device can operate to relieve anxiety, insomnia and depression similar to the CES device by employing the ear clip electrodes instead of the probe electrodes applied to other parts of the patient's body.

BRIEF DESCRIPTION OF THE DRAWINGS

For a better understanding of the invention and to show how the invention may be carried to effect, reference will now be made, purely by way of example, to the accompanying drawings in which.

DETAILED DESCRIPTION OF THE PRESENT INVENTION

The present invention used to treat anxiety, insomnia, depression and pain provides a safe, effective and proven alternative to drugs, especially in disorders that require long term management. Side effects of drugs are avoided, including accidental, intentional or suicidal overdoses. After treatment, there are usually no physical limitations proposed allowing the patient to resume normal activities. The treatment will be described is simple and can be easily self-administered at any time. Patients generally report a pleasant, relaxed feeling of well-being accompanied by an alert mind. The MET device would utilize probes described in U.S. patent application Ser. No. 12/219,878, which are held by the patient in place or through use of self-adhesive electrodes for pain control. Alternatively, when used for anxiety, insomnia and depression, ear clip electrodes will be employed. During a treatment, the patient may experience a mild tingling sensation at the electrode site. The use of the MET and CES devices can be added to other therapy prescribed by the patient's doctor and will not interfere with most other treatments with the exception that they may reduce the requirements for some medication.

Figure 1:
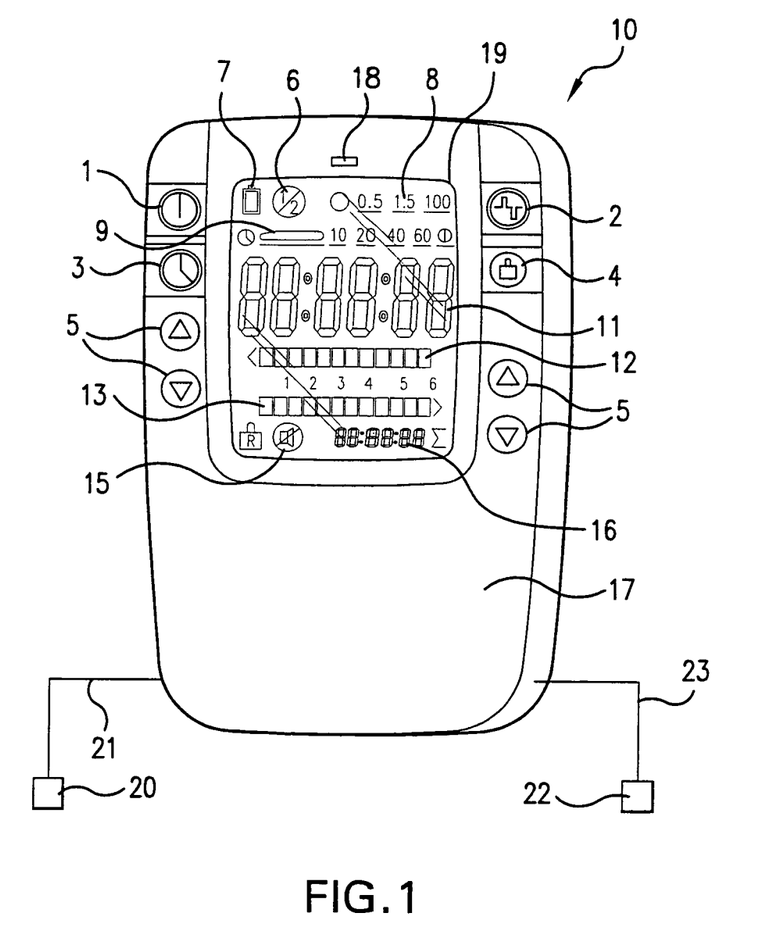
FIG. 1 is a drawing of the MET device.

The MET device 10 is illustrated in FIG. 1. This device is provided with a casing 17 into which the various electronic circuits used to produce the required waveforms are protected during use. Generally, the casing 17 would be constructed from a durable material such as a hard plastic to protect the contents. A display 19 is provided allowing the patient to monitor the operation of the MET device as well as to display various settings that the patient would apply utilizing the various input devices shown on either side of the display 19. Although the present invention operates utilizing an internal source of power, such as batteries, it can be included with a cord and a standard power adapter to be physically plugged into other sources of power such as an electrical outlet.

An ON/OFF switch 1 is provided to initially power the MET device as well as to turn the device off. Once the device is powered, various parameters of the operation of the device can be programmed. Generally, once these parameters are programmed, they will remain as a default setting not requiring the patient to initially set these parameters prior to each therapeutic use.

One of these parameters is the frequency of the waveform that is to be applied to the patient. This frequency is changed utilizing input device 2. As shown by the display 19, the patient is allowed to change the frequency applied to both outputs or channels, each channel of which is connected to a single probe either 20 or 22 which will be applied to the body either by a hand held probe, a self-adhesive probe or an ear clip electrode. The probe 20 is connected to the internal wave producing device utilizing a standard wire 21 and the probe 22 is connected to the internal wave producing device by a wire 23. It is noted that the frequency that is set into the input device 2 would be applied to both of the probes or electrodes 20, 22. It is noted that 0.5 Hz is the strongest frequency setting and the frequency that most individuals would utilize for the best results for all applications. However, as shown by the display 8, other settings such as 1.5 or 100 Hz for both channels may be used. Although the display 8 shows the use of 0.5, 1.5 or 100 Hz, the specific output frequencies generated by the MET device could be changed and various numbers of frequency settings may be employed. Prior to utilizing the device, input device 3 would be used to set the time period that the MET device would be operational. Although the exact time increments that could be programmed by the individual can change, the display 9 shows increments of 10, 20, 40 or 60 minutes. Once both of the probes 20 and 22 are applied to the skin, a waveform cycle would be initiated. Although it is not crucial to the present invention, a ten second repeatable waveform cycle may be employed.

The individual patient is given the ability of increasing or decreasing the current for each of the channels or probes separately utilizing up/down input devices 5, each of which is provided on either side of the display. The MET device can range from 0 to 600 microamperes for each of the channels. It is important to note that while the frequency generated for each of the channels is always equal to one another, the current levels for the channel can differ. Thereby, utilizing the up/down input devices 5, the amount of current applied to each probe can differ. The total amount applied to these channels are displayed utilizing the bar graphs 12, 13. Generally, the pressing of one of the input devices 5 would increase at 50 microampere intervals or decrease at 100 microampere intervals. It can be appreciated that the amount of microamperes would be increased or decreased by the depression of the input devices 5 could be altered.

A lock input device 4 is used to lock or unlock the setting during the treatment period if desired. Once the parameters are inputted into the device, it is important that they not be altered accidentally by the patient. Therefore, if the input device 4 is pressed at various intervals, such as twice within five seconds, the parameters would either be locked or unlocked.

The display could include various illumination devices, such as LEDs or LCDs. If an LCD screen is utilized, a light sensor 18 would sense the light of the surroundings and would illuminate the screen for an appropriate time such as 10 seconds when the device is used in a darkened environment. The screen would illuminate before this period of time, such as 10 seconds when any of the input buttons would be depressed.

It is important that both the probes 20, 22 be in contact with the skin. Therefore, as will be subsequently explained, circuitry is provided to insure that proper contact of the probes 20, 22 has been maintained. If this does not occur, display 6 would illuminate either the number 1 corresponding to the first channel, the number 2 corresponding to the second channel, or both 1 and 2 if neither of the probes is in proper contact with the skin. Additionally, an audio warning could be produced. If this occurs, the timer will stop and shut down for a period of time, such as 30 minutes if the situation has not been alleviated. The current must be set to be greater than 0 microamperes and moistened electrodes must be in contact with the skin for the MET device to operate properly. An audible output and the resumption of the timer as shown by display 11 would occur the instant that the integrity check circuit provided for the MET device determines that the device is now working properly. Additionally, it is noted that display 11 would display the amount of time that has elapsed after the start of the treatment period.

As previously indicated, the MET device would be operated utilizing one or more batteries. Therefore, a battery charge indicator 7 having a plurality of bars thereon would illustrate the state of the battery. For example, if the battery was totally charged, all of the bars would be displayed. As the battery loses its charge, more and more of the bars would not be illuminated. Therefore, it would behoove the individual to replace the battery at this point. An audible indication would also be generated when the battery charge level is low. It is noted that if the individual does not wish to hear any of the audible warnings, through the utilization of a series of inputs, the audible indication would be muted. When this occurs, the mute indicator 15 would become illuminated.

Finally, a cumulative timer 16 would display the total hours and minutes that the MET device has been utilized.

The operation of the MET device will now be described. Prior to use, the skin around the treatment area is cleaned before applying the electrodes. This is done utilizing mild soap and water, rinsing the area and allowing the skin to dry thoroughly. This is important especially around areas where skin oils or dirt have accumulated, or where cosmetics or hair spray have been used. If skin irritation develops, discontinue the use of the MET device. Additionally, varying the particular electrode location on the body may also help to minimize skin irritation.

When utilizing the MET device to relieve pain, the patient should evaluate the pain they are experiencing before, during the treatment and after each treatment. A simple guideline in which the intensity of the pain is evaluated based upon a numeric guideline can be utilized. This guideline would cover, for example, assigned values of the pain intensity from 0 to 10 wherein 0 indicates no pain and 10 is the maximum pain scale at the beginning and end of each treatment. It is also helpful to utilize these parameters during the treatment session. Keeping a daily, or even an hourly chart of the changes in the pain level on the 1 to 10 scale will assist the healthcare practitioner to give the patient the best possible device. However, it is important to note that due to the low level of current applied to a patient's body through the use of the various types of electrodes, many patients would not feel anything. During the treatment, it is important to note that as previously described, the MET device would be working properly unless the indicator 6 as shown in FIG. 1 would display the number 1 or 2 for the particular channel that might not be operating properly. Once the probes are plugged into the MET device, the ON/OFF switch 1 would be depressed. At this point, the patient would set the frequency to 0.5 Hz or a desired setting. For example, where joint problems such as shoulders, elbows, wrists, fingers, hips, knees, ankles, toes, the 100 Hz setting should be used for approximately 10 to 20 seconds immediately followed by the 0.5 Hz setting. If this is not effective, the 1.5 Hz setting should be utilized. Additionally, the correct time of the treatment should be set utilizing the timer input device 3 and the current levels should be used using the input devices 5 of each channel. It is recommended that each channel be set to 600 milliamperes. If this setting feels uncomfortable to the patient, it should be decreased immediately. Additionally, if the patient feels dizziness or nausea develops, the current value should also be decreased. It is important to note that both of the probes should be used together to complete the electric circuit. The treatment is continued until pain is completely gone or maximum relief is achieved. At this point, the power is turned off and cranial electrotherapy simulation should then be utilized by the patient. These steps should be repeated as necessary.

Figure 4:
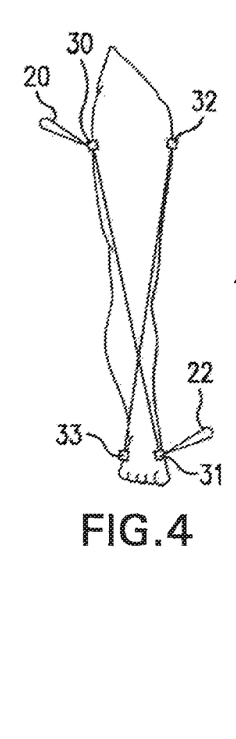
FIGS. 4-10 are drawings showing the placement of the electrode used with the MET device to treat various pain locations.
Figure 5:
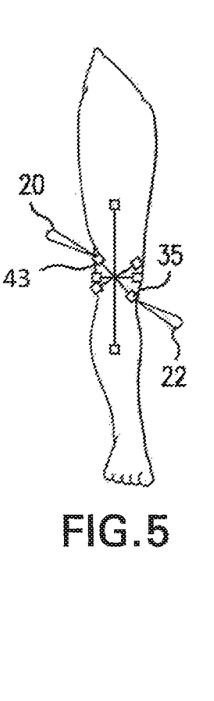
Figure 6:
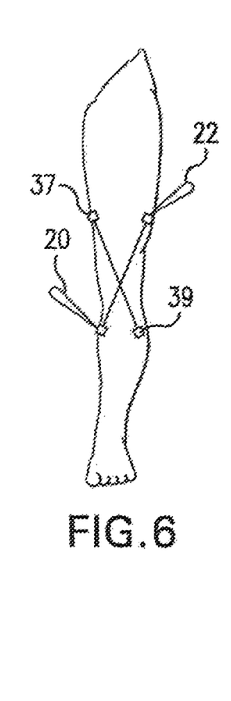
Figure 7:
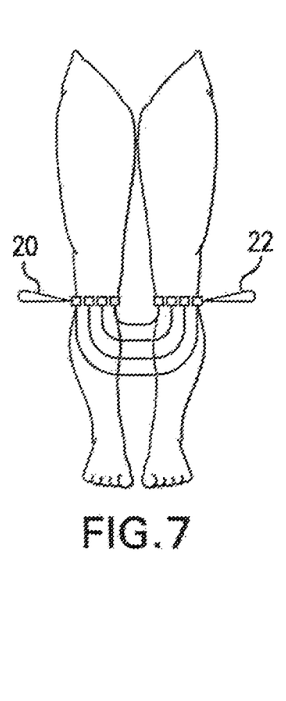

The proper placement of the electrodes during the pain treatment using the MET device for various portions of the body are shown in FIGS. 4-10. For example, when treating a patient for knee pain, the treatment area should extend for the entire length of the leg. In this instance, as shown in FIG. 4, one probe 20 is placed on location 30 above the knee and the second probe 22 is placed on location 31 on the patient's foot. The location of the probe 20 can then be changed to location 32 and the location of probe 22 could then be changed to location 33 for a period of time. The treatment would then extend to an area closer to the knee as shown in FIG. 5 in which the probe 20 is placed on location 43 and the probe 22 is placed on location 35. As the treatment progresses, the probes 20 and 22 would then be moved: to the various oilier locations as denoted by the black boxes shown in FIG. 5. It is important to note that the probes must always be placed on opposite sides of the body. The treatment would continue as shown in FIG. 6 by placing the probe 20 below the knee and the probe 22 above the knee. During this portion of the treatment, the probe 20 would then moved to location 37 located above the knee and the probe 22 be placed in location 39 below the knee. The treatment would then continue by placing the probe 20 below the treatment area and the other probe 22 in the same place on the opposite side of the body. Shown in FIG. 7, the probe 20 would then be moved to other locations on a line below the knee as will probe 22. This would direct the current through the nerves and the spinal cord of the body. These treatment steps would be repeated as necessary, varying the probe positions but always directing the current between the probes to the area being treated. The treatment would be continued until the pain is fully gone or maximum relief is achieved.

Figure 8:
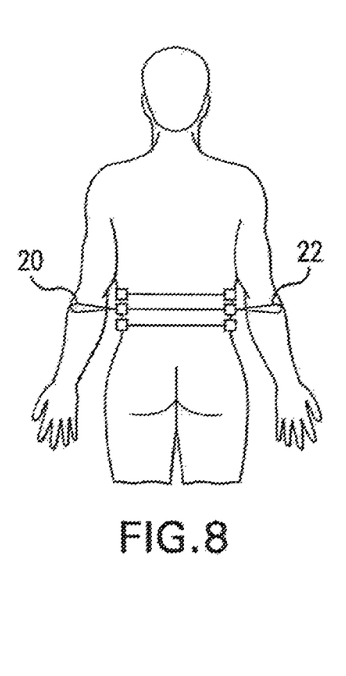

For back pains, the probes 20 and 22 should be placed in at least three locations on both sides of the body at the level being treated and slightly above and below this level as shown in FIG. 8.

Figure 9:
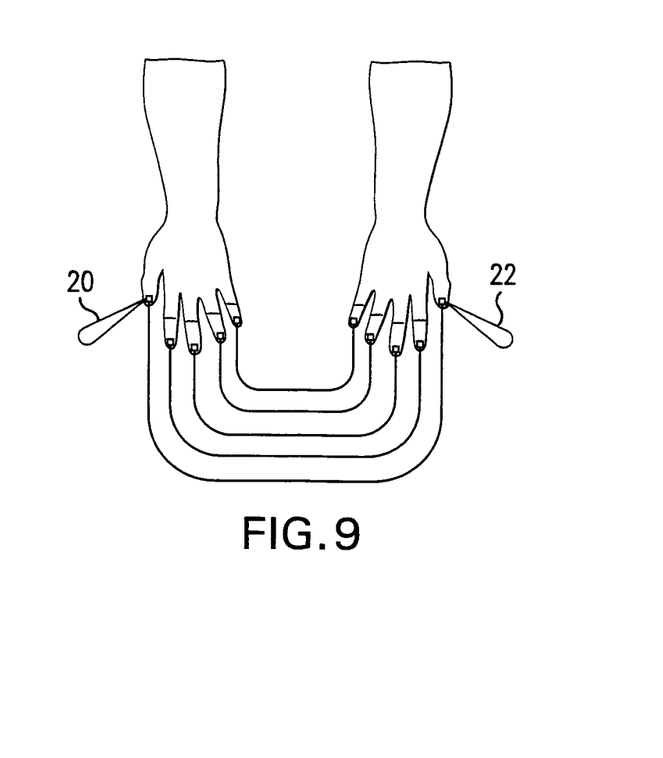
Figure 10:
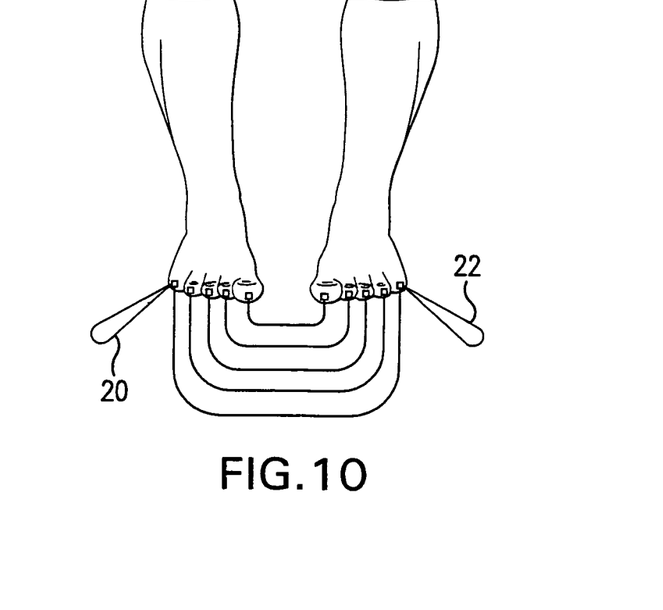

FIGS. 9 and 10 show the strategy for treating various problems by connecting one of the probes 20 as shown in FIG. 9 to one fingertip and the other probe 22 to the same finger on the opposite hand for approximately 10 to 20 seconds. Each probe 20, 22 would then be moved to the next finger or toe as shown in FIG. 10.

As previously discussed, cranial electrotherapy simulation (CES) is used to treat anxiety, insomnia, and depression in which the ear clip electrodes 20, 22 are attached to both of the ear lobes of the patient. After the power is engaged, the frequency is set to preferably 0.5 Hz. If this is not effective, one of the other settings should be utilized. Additionally, the timer is generally set to 20 minutes and the current is set to at least 250 microamperes. One hour is recommended if the current is at or below 200 microamperes. If no setting is inputted, the current would default to 100 microamperes when the device is turned on. Current should then be increased slowly until a dizzy feeling is experienced, like rocking on a boat and decreases immediately until this dizziness ceases. The power would then cease after the conclusion of the timed cycle. It is important to always complete a CES session. When this session ends, if a heavy feeling is still experienced, treatment should be resumed until at least two minutes after the heaviness lifts and a light feeling develops. Failure to do this can result in disorientation that can last for hours to days. It is recommended that current levels on both channels be equal and not greater than 500 microamperes.

Figure 2:
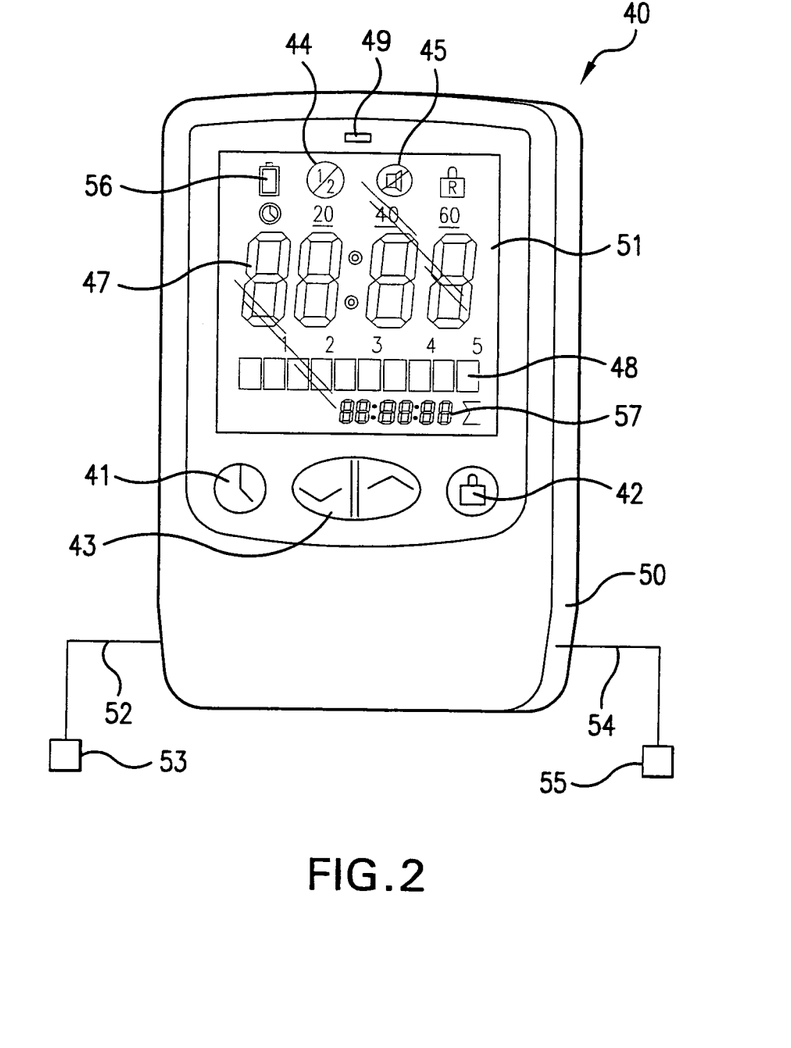
FIG. 2 is a drawing of the CES device.
Figure 3:
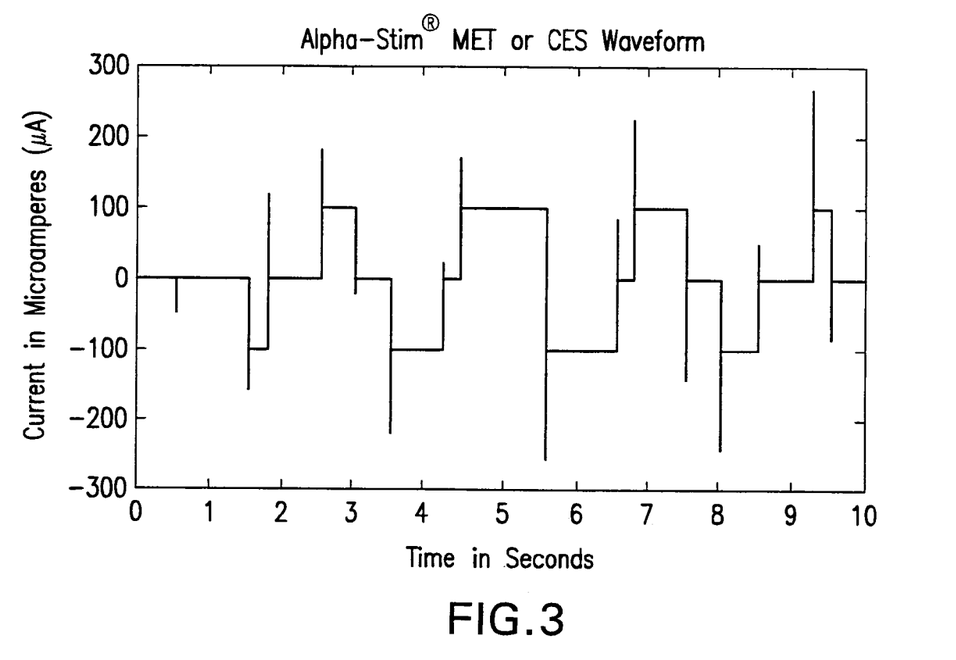
FIG. 3 is a typical waveform generated by both the MET and CES device.

FIG. 2 illustrates a device 40 used to control anxiety, insomnia and depression but not pain. This device 40 produces a modified square-bipolar waveform of 0.5 pulses per second at 50 to 500 microamperes in a 50% duty cycle as shown in FIG. 3. This figure also shows the typical wave pulse for the MET device. The device 40 includes a durable case 50 similar to the MET device and also includes a display area 51. Although not shown, the device would include an ON/OFF switch. Once this switch is engaged, a timer 41 is used to set a particular treatment time, such as 20, 40 or 60 minutes as shown in the display. Only a single current output is provided and is transmitted to both of the ear clip electrodes connected to the patient's ear lobes. Each ear clip electrode 53,55 is connected to the CES device 40 through the use of appropriate wires 52, 54. Current to each of the ear clip electrodes would be set utilizing an input device 43 which increases or decreases current from a default value of 100 microamperes. The device would increase the current level at 50 microampere increments per second and would decrease it at 100 microamperes per second. The countdown of the treatment time would be shown utilizing the display 47. An input device 42 is used to lock or unlock any of the settings. Similar to the MET device, the CES device would include a light sensor 49 for illuminating the LCD screen for a period of time, such as 10 second when the device is used in a darkened room. If the ear clips are not properly attached to the patient's ears or the device is not operating properly for any other reason based upon a diagnostic testing application, symbol 44 would be illuminated as well as an audio symbol would be produced. Similar to the MET device, the CES device is generally battery operated and the charge of the battery would be illustrated by icon 56. Icons 48 would indicate the amount of microamperes to which the device has been set. A mute fix feature 45 is used to indicate whether any audio output will be heard. Finally, a cumulative timer 57 would be utilized to show the total amount of treatment time that the CES device has been used.

The CES device to treat anxiety, insomnia and depression with ear clip electrodes would operate in a manner similar to the MET device and there is no need to repeat the manner of use of the CES device. During usage, the anxiety reduction is usually experienced during a single treatment, but may be seen hours after treatment. Insomnia is usually improved after one treatment to three weeks of use. Depression typically takes three to six weeks or more of daily treatment to improve this condition, but may take a considerably longer time. After the condition is under complete control, the CES device should be used two or three times a week to maintain good results.

FIG. 3 illustrates a typical waveform produced by both the MET or CES devices. This waveform is produced by a waveform generator in which the various aforementioned parameters, such as the current and the frequency are inputted to the MET or CES devices as previously described.

Figure 11:
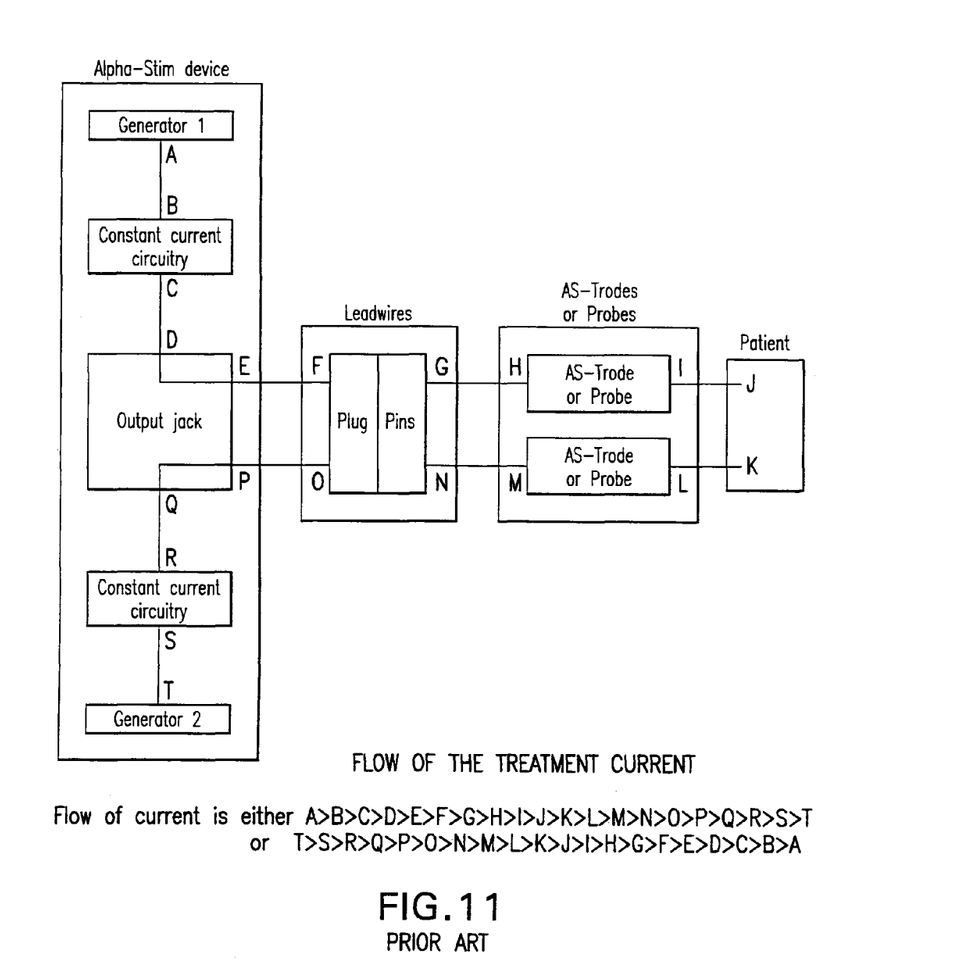
FIG. 11 is a circuit diagram showing a prior art device for applying waveforms to the body.
Figure 12:
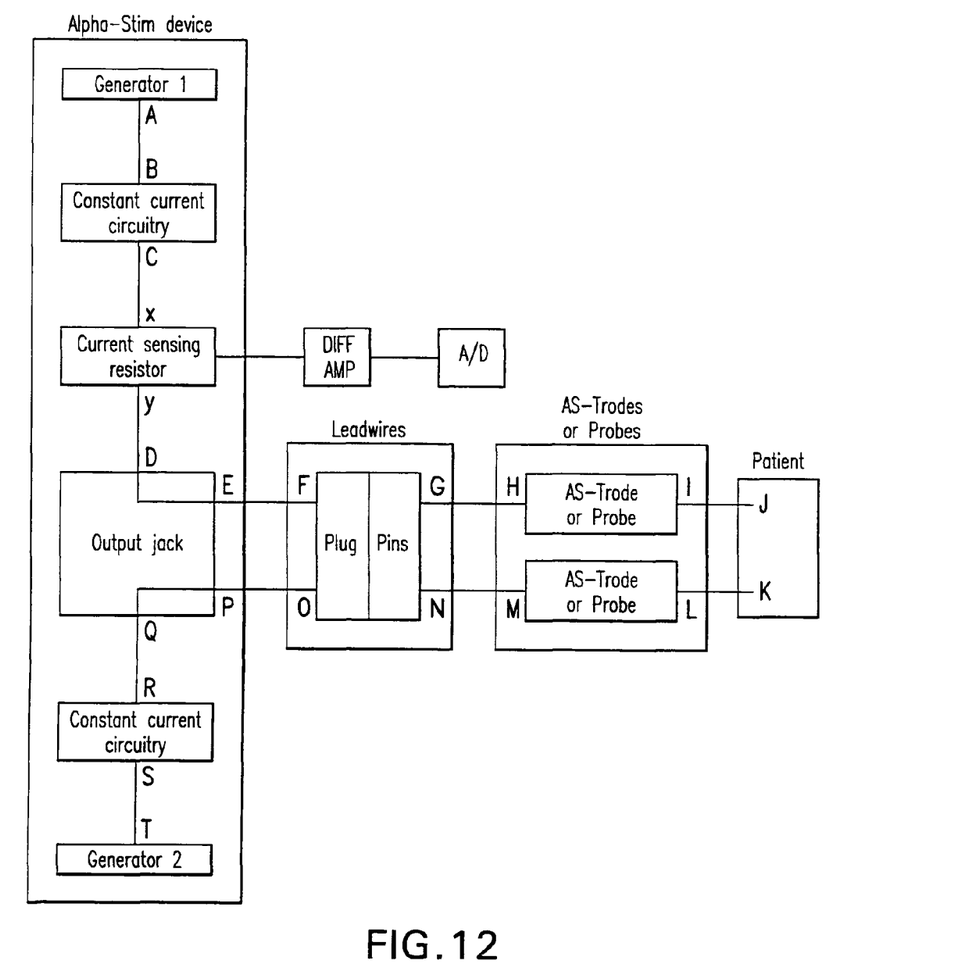
FIG. 12 is a block diagram showing the circuitry of the present invention.

FIG. 11 illustrates a block circuit diagram of a prior art circuitry, wherein FIG. 12 shows the circuitry utilized by the present invention. The main difference between these circuits is the inclusion of the current sensing resistor, the differential amplifier and an analog to digital converter shown in FIG. 12.

Each of these circuits includes two waveform generators. When waveform generator 1 is at a logic HIGH level and the waveform generator 2 is a logic LOW level, treatment current flows through the patient in one direction i.e. from node J to node K as illustrated by the first expression under "FIG. 11, Flow of the treatment current". When the waveform generator 1 is a logic LOW level and the waveform generator 2 is at a logic HIGH level, the treatment current flows through the patient in the other direction i.e. from node K to node J as illustrated by the second expression under "FIG. 11, Flow of the treatment current."

Because of the use of the constant current sources, additional current sensing resistors have no affect on the treatment current provided that the value of the current sensing resistor is small compared to the impedance of the treatment site. Therefore, when current flows through the current sensing resistor, according to Ohm's Law, a voltage drop will develop across the resistor. The magnitude of this voltage drop is proportional to the current that flows through the resistor. If the treatment current is zero, the voltage drop would be zero. A differential amplifier and an analog-to-digital converter shown in FIG. 12 would act as a voltmeter circuit to measure the magnitude of the voltage drop across the current sensing resistor. The input impedance of this voltmeter circuit is designed to be very high compared to the impedance of the treatment site. Therefore, this additional voltmeter circuitry has no effect on the treatment current. However, if one or both of the electrodes are not connected to the body of the patient, a circuit discontinuity would occur at node G, N, J and/or node K and no current can flow at any point in the output circuitry of either FIG. 11 or 12 including the current sensing resistor. Therefore, if one of the electrodes is no longer in contact with the patient's body, the voltmeter circuitry would read an output of zero indicating the displacement of one or both of the electrodes. This displacement would be illustrated by the icon 6 shown in FIG. 1 or the icon 44 shown in FIG. 2. Conversely, if the voltmeter circuitry is not zero, then both of the electrodes are still on the body of the patient.

The present invention may be embodied in other specific forms without departing from the spirit or central characteristics thereof. Present embodiments are therefore to be considered in all aspects as illustrative but not restrictive, the scope of the invention being indicated by the appended claims rather than by the foregoing description, and all changes which come within the meaning and range of equivalents of the claims are therefore intended to be embraced therein.

What is claimed is:

1. An electromedical device for producing electrical waveforms to be introduced into an individual's body for treating pain, anxiety, insomnia and depression, comprising:
    a first waveform generator producing a first electrical waveform having a current and frequency said first electrical waveform including a series of positive and negative pulses and a series of positive and negative spikes, each of said positive pulses directly following a positive spike, and each of said negative pulses directly following a negative spike, wherein said first electrical waveform pierces the skin resistance to drive said positive and negative pulses into the individual's body;
    first and second electrodes in communication with said waveform generator for contact with the individual's skin, thereby introducing said electrical waveform into the individual's body for transmission to the individual's brain;
    a device for setting the frequency of said first electrical waveform; and
    a device for setting the current of said first electrical waveform,
        wherein, applying said electrical waveform to the body of the individual would treat pain, anxiety, insomnia and depression.

2. The electromedical device in accordance with claim 1, wherein said first and second electrodes are ear clip electrodes applied to the ear lobes of the individual.

3. The electromedical device in accordance with claim 1, wherein said first electrical waveform has a current less than 500 microamperes, and said first and second electrodes are applied to the individual's body, whereby anxiety, insomnia and depression are treated.

4. The electromedical device in accordance with claim 1, further including a second waveform generator producing a second electrical waveform, said second electrical waveform including a series of positive and negative pulses and a series of positive and negative spikes, each positive pulses directly following a positive spike, and each negative pulses directly following a negative spike, said second waveform generator provided with a device for setting the frequency of said second electrical waveform, and a device for setting the current of said second electrical waveform, wherein said first electrical waveform is connected to said first electrode and said second electrical waveform is unequal in frequency and/or current from said first electrical waveform, said second electrical waveform connected to said second electrode, wherein said second electrical waveform pierces the skin resistance to drive said positive and negative pulses into the individual's body.

5. The electromedical device in accordance with claim 1, further comprising a current sensing resister and voltmeter provided between said first waveform generator and said first and second electrodes for sensing whether either or both of said electrodes are not in contact with the skin of the individual during operation of the device.

6. The electromedical device in accordance with claim 5, further including a display for indicating that one or both of said first and second electrodes are not in contact with the skin.

7. The electromedical device in accordance with claim 1, including a timer for setting a treatment timer, said timer including a visual display.

8. The electromedical device in accordance with claim 4, wherein both of said first and second electrical, waveforms have a frequency of 0.5 HZ.

9. The electromedical device in accordance with claim 4, wherein each of said first and second waveforms have a current of less than 600 microamperes to treat pain, and wherein each of said first and second electrodes are applied to the body below the neck.

10. The electromedical device in accordance with claim 1, wherein said first electrical waveform has a current less than 600 microamperes, and said first and second electrodes are applied to the individual's body below the neck, whereby pain is treated.

* * * * *

UNITED STATES PATENT AND TRADEMARK OFFICE
CERTIFICATE OF CORRECTION

| | | |
|---|---|---|
| PATENT NO. | : 8,612,008 B2 | Page 1 of 1 |
| APPLICATION NO. | : 12/588647 | |
| DATED | : December 17, 2013 | |
| INVENTOR(S) | : Daniel L. Kirsch and Sai Cheong Chan | |

It is certified that error appears in the above-identified patent and that said Letters Patent is hereby corrected as shown below:

In the Claims

Column 10, line 31, cancel the text beginning with "8. The electromedical device" to an ending "of 0.5 HZ.", and insert the following claim:

--8. The electromedical device in accordance with claim 4, wherein both of said first and second electrical waveforms have a frequency of 0.5 HZ.--

Signed and Sealed this
Twenty-fifth Day of February, 2014

Michelle K. Lee
*Deputy Director of the United States Patent and Trademark Office*